United States Patent [19]

Ling

[11] Patent Number: 5,037,805
[45] Date of Patent: Aug. 6, 1991

[54] METHODS OF CONTRACEPTION

[75] Inventor: Nicholas C. Ling, San Diego, Calif.

[73] Assignee: The Salk Institute for Biological Studies, San Diego, Calif.

[21] Appl. No.: 326,151

[22] Filed: Mar. 20, 1989

[51] Int. Cl.[5] ...................... A61K 37/43; C07K 13/00
[52] U.S. Cl. ......................................... 514/8; 514/21; 530/395; 424/85.8
[58] Field of Search .................... 514/8, 21, 2, 3; 530/395; 424/85.8

[56] References Cited

U.S. PATENT DOCUMENTS 4,734,398  3/1988  DiZerega .............................. 514/2
4,764,502  8/1988  DiZerega .............................. 514/2

OTHER PUBLICATIONS

DiZerega et al., "Identification of Protein(s) Secreted by the Preovulatory Ovary which Suppresses the Follicle Response to Gonadotropins," *J. Clin. Endocrinol. & Metabolism*, 56(1): 1091–1096 (1983).

DiZerega et al., "Activity of a Human Follicular Fluid Protein(s) in Spontaneous and Induced Ovarian Cycles," *J. Clin. Endocrinol. & Metabolism*, 57(4): 838–846 (1983).

DiZerega et al., "Identification of Proteins in Pooled Human Follicular Fluid which Suppress Follicular Response to Gondadotropins," *J. Clin. Endocrinol. & Metabolism*, 54(6): 35–41 (1983).

DiZerega et al., "Human Granulosa Cell Secretion of Protein(s) which Suppress Follicular Response to Gonadotropins," *J. Clin. Endocrinol. & Metabolism*, 56(1): 147–155 (1983).

Kling et al., "Identification of a Porcine Follicular Fluid Fraction which Suppresses Follicular Response to Gonadotropins," *Biology of Reproduction*, 30: 564–472 (1984).

Ono et al., "Biochemical and physiologic characterization of follicle regulatory protein: A paracrine regulator of folliculogenesis," *Am. J. Obstet. Gynecol.*, 709–716, Apr. (1986).

Wood et al., "Cloning and Expression of the Growth Hormone-Dependent Insulin-Like Growth Factor-Binding Protein," *Molecular Endocrinology*, 2(12): 1176–1185 (1988).

Baxter et al., "Binding Proteins for Insulin-Like Growth Factors in Adult Rat Serum.," *Biochem. & Biophyl. Res. Comm.*, 147(1): 408–415, Aug. 31, 1987.

*Primary Examiner*—Jeffrey E. Russel
*Assistant Examiner*—Kay Kim
*Attorney, Agent, or Firm*—Fitch, Even, Tabin & Flannery

[57] ABSTRACT

Methods are disclosed for regulating ovulation or fertility in female mammals, for regulating spermatogenesis in males and for treating conditions such as endometriosis. Administration of effective amounts of an FSH-Inhibiting Protein (FSH-IP) can be used for female contraception and also for male contraception by preventing sperm production. FSH-IP, in its native form, is a glycosylated protein having an apparent molecular weight of about 50,000 Daltons (50kD) which inhibits the production of estradiol that would otherwise be stimulated by FSH in certain cells, such as granulosa cells. Antibodies to these FSH-IP proteins, preferably of monoclonal form can be produced using techniques presently known in the art and are useful for treatment to promote ovulation or superovulation in mammals, including humans and livestock.

2 Claims, 4 Drawing Sheets

METHODS OF CONTRACEPTION

This invention was made with Government support under NICHD Contract No. NO1-HD-6-2944 and grants HD-09690 and DK-1811 from the National Institutes of Health. The Government has certain rights in this invention.

This invention relates to the regulation of fertility, and more particularly to methods for male and female contraception using proteins which block the effect of FSH at the ovaries and testes and thereby prevent FSH from carrying out its normal function in the gonad.

BACKGROUND OF THE INVENTION

It is known that FSH is required for the maturation of ovarian follicles and testicular spermatogenesis, and that, in adults, circulating FSH regulates gonadal differentiation and steroidogenesis. However, increases in ovarian follicle growth are not always correlated with elevations of FSH levels in circulating blood serum. It is also known that a particular ovarian follicle that is destined to ovulate is derived from a fairly large number of growing follicles which are, in turn, selected from a still larger group of nonproliferating primordial follicles formed during fetal development. As a result, it is concluded that there is some selection process by which, during each ovarian cycle, one of these follicles destined to ovulate is activated.

It has previously been postulated that there are proteins which suppress follicular response to gonadotropins such as FSH: diZerega et al., *J. of Clin. Endocrinol. Metab.*, 56, 1, 35-41 (1983), *J. of Clin. Endocrinol. Metab.*, 57, 4, 838-846 (1983), and *J. of Clin. Endocrinol. Metab.*, 54, 6, 1091-1096 (1982). It was hypothesized by these investigators that the dominant follicle may be secreting a substance that suppressed the responses of the other follicles to the FSH: diZerega et al., *J. Clin. Endocrinol. Metab.*, 56, 4, 147-155 (1983).

Further work in this area caused investigators to postulate that a protein, termed generically a follicle regulatory protein, was apparently present in a crude or partially purified extract from porcine follicular fluid which would delay follicular maturation and would inhibit the effects of FSH in some manner, Kling et al., *Biology of Reproduction*, 30, 564-572 (1984) and Ono et al., *Am. J. Obstet. Gynecol.*, 154, 4, 709-716 (1986). Subsequently, U.S. Pat. Nos. 4,734,398 and 4,764,502 were issued directed to such extracts and stating that there were contained therein proteins between 5,500 and 18,000 daltons which exhibited such an effect. Although these partially purified extracts were useful for such in vitro studies, it is recognized that a pure material is necessary for clinical applications.

SUMMARY OF THE INVENTION

It has now been found that both male and female contraception can be carried out by administering a protein which has been isolated from ovarian follicular fluid, purified to homogeneity and partially characterized, which protein can inhibit the follicular response to gonadotropins and, more specifically, inhibit the production of estrogens that would otherwise be stimulated by FSH in certain cells, such as granulosa cells. Thus, the protein is useful in male and female contraception because germ cell maturation requires FSH stimulation.

The protein in question of the porcine species has an apparent molecular weight of about 50,000 Daltons (50 kD) in its native glycosylated form; however, a substantial portion of this apparent molecular weight is believed to be attributed to glycosylation. The amino terminal sequence of the protein is as follows: Gly-Ser-Gly-Ala-Val-Gly-Thr-Gly-Pro-Val-Val-Arg-Cys-Glu-Pro-Cys-Asp-Ala-Arg-Ala-Leu-Ala-Gln-Cys-Ala-Pro-Pro-Pro-Ala-Ala-Pro-Pro-Cys-Ala-Glu-Leu -Val-Arg-Glu-Pro-Gly-Cys-. It is believed that the protein has about 260 to 270 amino acid residues.

The foregoing N-terminus information is sufficiently specific that oligonucleotide probes can be prepared which can effectively determine the complete primary structure of the protein via molecular cloning based upon a porcine cDNA library. Moreover, either the same probes, or probes in the form of segments from the cloned porcine DNA, will be sufficient to allow the straightforward determination of homologous sequences of this protein, termed FSH-Inhibiting Protein (FSH-IP), of other mammalian species, in view of the previously demonstrated homology between the hormones of this type in the various mammalian species.

In fact, oligonucleotide probes based upon the N-terminal amino acid sequence of the homologous human protein were recently prepared and were used to screen a human cDNA library and resulted in obtaining independent cDNA clones containing exactly the same sequences (W. Wood et al., *Molecular Endocrinology*, 2, 12, 1176-1185, 1988). As a result, the amino acid sequence of human FSH-IP has been established as having the following 264-residues: G A S S G G L G P V V R C E P C D A R A L A Q C A P P P A V C A E L V R E P G C G C C L T C A L S E G Q P C G I Y T E R C G S G L R C Q P S P D E A R P L Q A L L D G R G L C V N A S A V S R L R A Y L L P A P P A P G N A S E S E E D R S A G S V E S P S V S S T H R V S D P K F H P L H S K I I I K K G H A K D S Q R Y K V D Y E S Q S T D T Q N F S S E S K R E T E Y G P C R R E M E D T L N H L K F L N V L S P R G V H I P N C D K K G F Y K K K Q C R P S K G R K R G F C W C V D K Y G Q P L P G Y T T K G K E D V H C Y S M Q S K wherein the below-indicated single letter designations are used to represent the individual amino acids.

| Asp | D | Aspartic acid | Ile | I | Isoleucine |
|---|---|---|---|---|---|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

These FSH-IP proteins are useful in regulating ovulation in mammals, e.g., they can be used as female contraceptives, and can also be used as male contraceptives to prevent sperm production. Moreover, antibodies to these FSH-IP proteins of either monoclonal or polyclonal form can be produced using techniques presently known in the art, and such antibodies can be elicited using only the synthetic N-terminal segment of the porcine protein disclosed hereinbefore which are effective to counteract the effects of FSH-IP. These antibodies can be used in assays for detecting the levels of FSH-IP in mammals, particularly humans. The antibodies can also be used for treatment to promote ovulation or superovulation in mammals, including humans and livestock. Thus, these antibodies should prove to be quite useful for diagnostic test kits and the like that will permit the diagnosis of a potential cause of infertility, e.g., gonadal dysfunction.

BRIEF DESCRIPTION OF THE DRAWINGS

FIG. 2 shows results from an Aquapore RP-300 semi-preparative column eluted with the TFA solvent system; FIG. 3 from a Vydac $C_4$ semi-preparative column with the triethylamine phosphate solvent system; and FIG. 4 from a Vydac $C_4$ semi-preparative column with the TFA solvent system. Shown superimposed upon all four figures are results of the in vitro bioassay, with the active zone being represented by a black bar.

DETAILED DESCRIPTION OF THE PREFERRED EMBODIMENTS

Mammalian FSH-IP was isolated from porcine follicular fluid and can be similarly isolated from other mammalian follicular fluids and from blood plasma, including human plasma. It was purified to substantial homogeneity using chromatographic separations. Thereafter, the pure material was subjected to Edman degradation in a gas-phase sequencer and was also subjected to gel electrophoresis in order to estimate the size of the molecule. Further testing shows that the protein binds to Concanavalin A, establishing that it is a glycoprotein. In its glycosylated form, it has a molecular weight in the range of between about 45,000 to about 50,000 kD and an isoelectric point of about 6. It is estimated that the porcine FSH-IP protein contains between about 260 and about 270 amino acid residues. The results of the gas-phase sequencing establishes that the N-terminus of porcine FSH-IP(pFSH-IP) has the following sequence:

Gly—Ser—Gly—Ala—Val—Gly—Thr—Gly—Pro—Val—Val—

Arg—Cys—Glu—Pro—Cys—Asp—Ala—Arg—Ala—Leu—

Ala—Gln—Cys—Ala—Pro—Pro—Pro—Ala—Ala—Pro—Pro—

Cys—Ala—Glu—Leu—Val—Arg—Glu—Pro—Gly—Cys—.

FSH-IP proteins can be obtained from mammalian follicular fluid using the isolation and purification processes set forth hereinafter. They can also be isolated from plasma and likely from other mammalian sera.

In order to eliminate most of the high molecular weight compounds and to dissociate the binding proteins from growth factors that are found in porcine follicular fluid, an ammonium sulfate precipitation process is first carried out, followed by dialysis in 30% acetic acid. More specifically, 250 milliliters of porcine follicular fluid is mixed with one liter of cold water containing 35 grams of ammonium sulfate in a cold room for about 2 hours to obtain a 5% saturated solution. The resulting solution is dialyzed in the cold room for 24 hours against 14 liters of 30% (v/v) acetic acid in water, with one change of the dialysis solvent, using Spectrapor No. 6 membrane tubing, 28.6 mm diameter, $M_r$ cutoff 1000, to remove the ammonium sulfate. The dialyzed retentate is then clarified by centrifugation (10,000 rpm, 30 min) to remove a white precipitate, and this dialyzed extract is lyophilized and then dissolved in 200 milliliters of 30% acetic acid.

Figure 1:
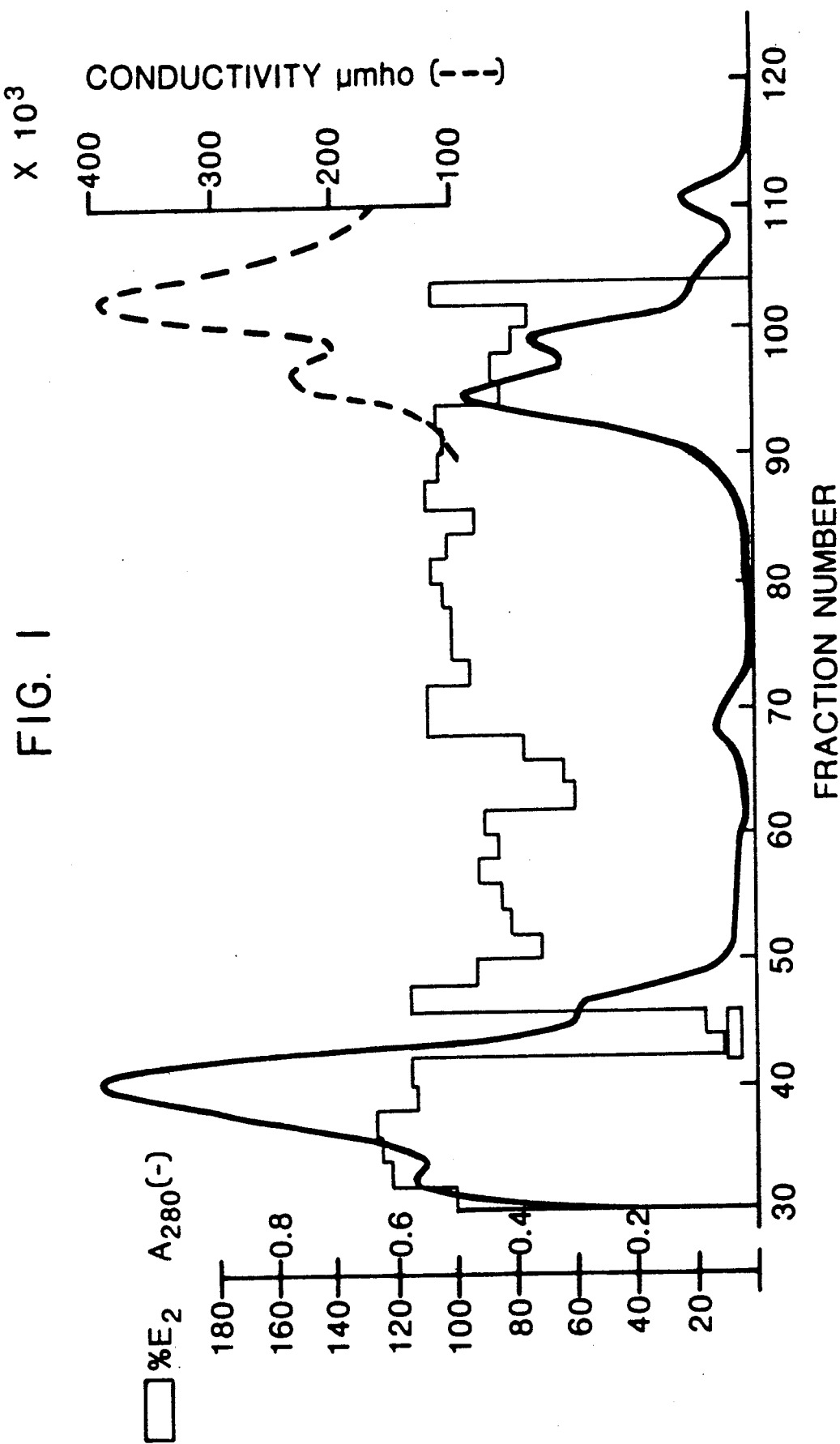
FIG. 1 shows purification on a Sephacryl S-200 column with elution by 30% acetic acid.

After further centrifugation to remove insoluble particles, the solution is divided into four equal volumes for loading onto four $5 \times 100$ cm columns of Sephacryl-200 superfine and eluted with 30% acetic acid at 20 ml/25 min at room temperature. Column fractions are collected and subjected to bioassay, using samples that are prepared by taking 0.2–1% aliquots of the column fractions in 1.5 ml Eppendorf tubes which are pre-coated with a compound that prevents adherence of the sample to the tube wall and which has no activity in the bioassay. One such coating peptide which has been used is an N-terminal, substituted fragment of the porcine inhibin alpha-chain, namely [$Arg^{14}$, $Tyr^{27}$]-pIn(1-27)$NH_2$. The bioassay, which is described in detail hereinafter, is one which monitors for estradiol production. Only one zone of potent inhibition of estradiol production is located which is denoted by a black bar in FIG. 1.

Figure 2:
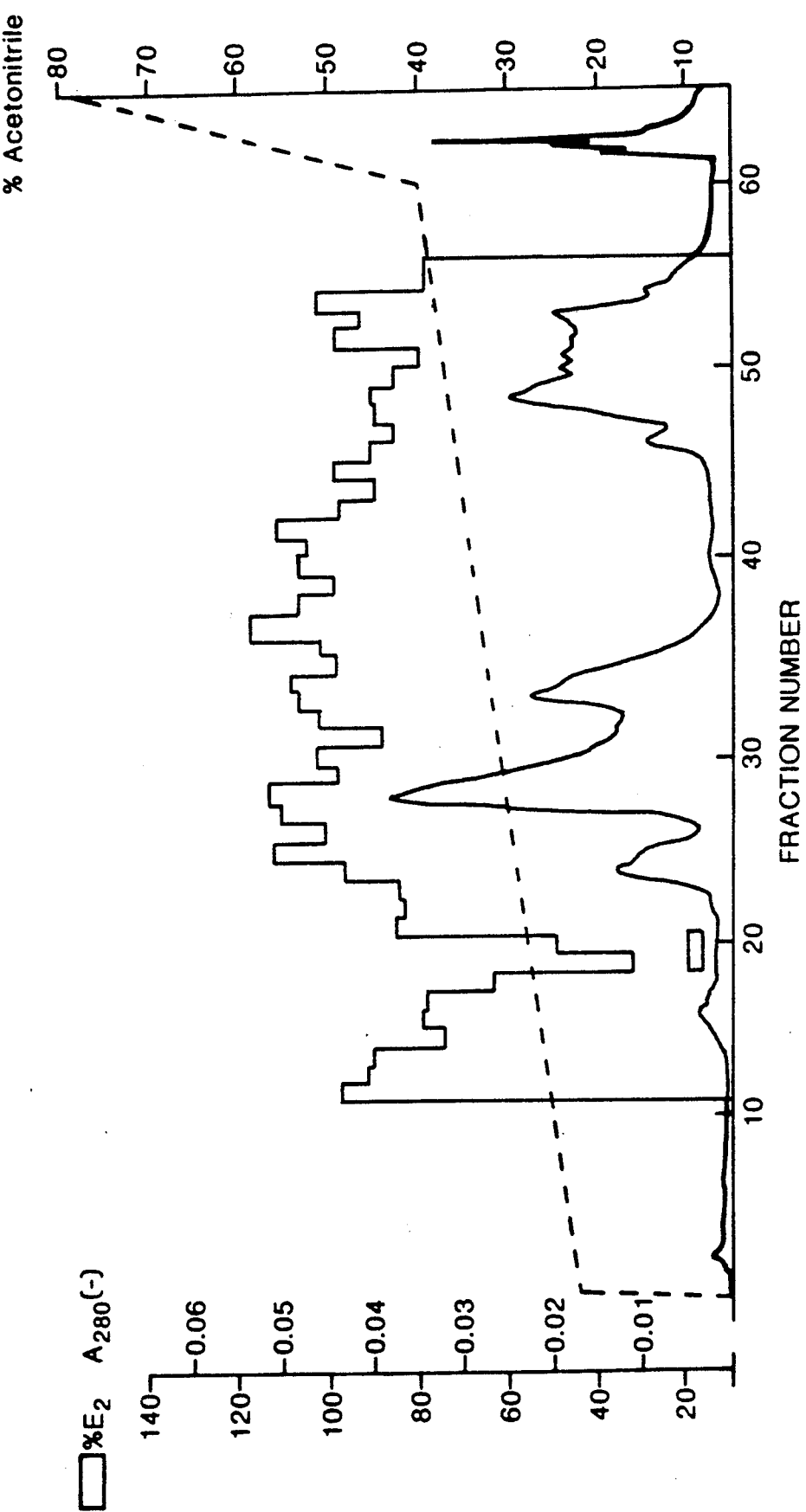
FIGS. 2, 3 and 4 show sequential RP-HPLC purification of the previously partially purified FSH-IP material.

The active fractions from the four columns are pooled and subjected to reverse phase HPLC purification on a Brownlee Aquapore RP-300 $0.7 \times 25$-cm $10\mu$, $C_8$ column. The protein from the Sephacryl fractionation chromatography is pumped onto the reverse phase column using 0.1% aqueous trifluoroacetic acid (TFA) as solvent and subsequently eluted at 3 ml/min with a 180 min. gradient of 22 to 40% acetonitrile with the remainder of solvent being 0.1% TFA. Fractions of 3 ml each are collected at room temperature using a back pressure of 980 psig and subjected to the same bioassay. Only one zone of activity is located, denoted by the black bar in FIG. 2, and these fractions are pooled and then diluted with 0.2M acetic acid.

Figure 3:
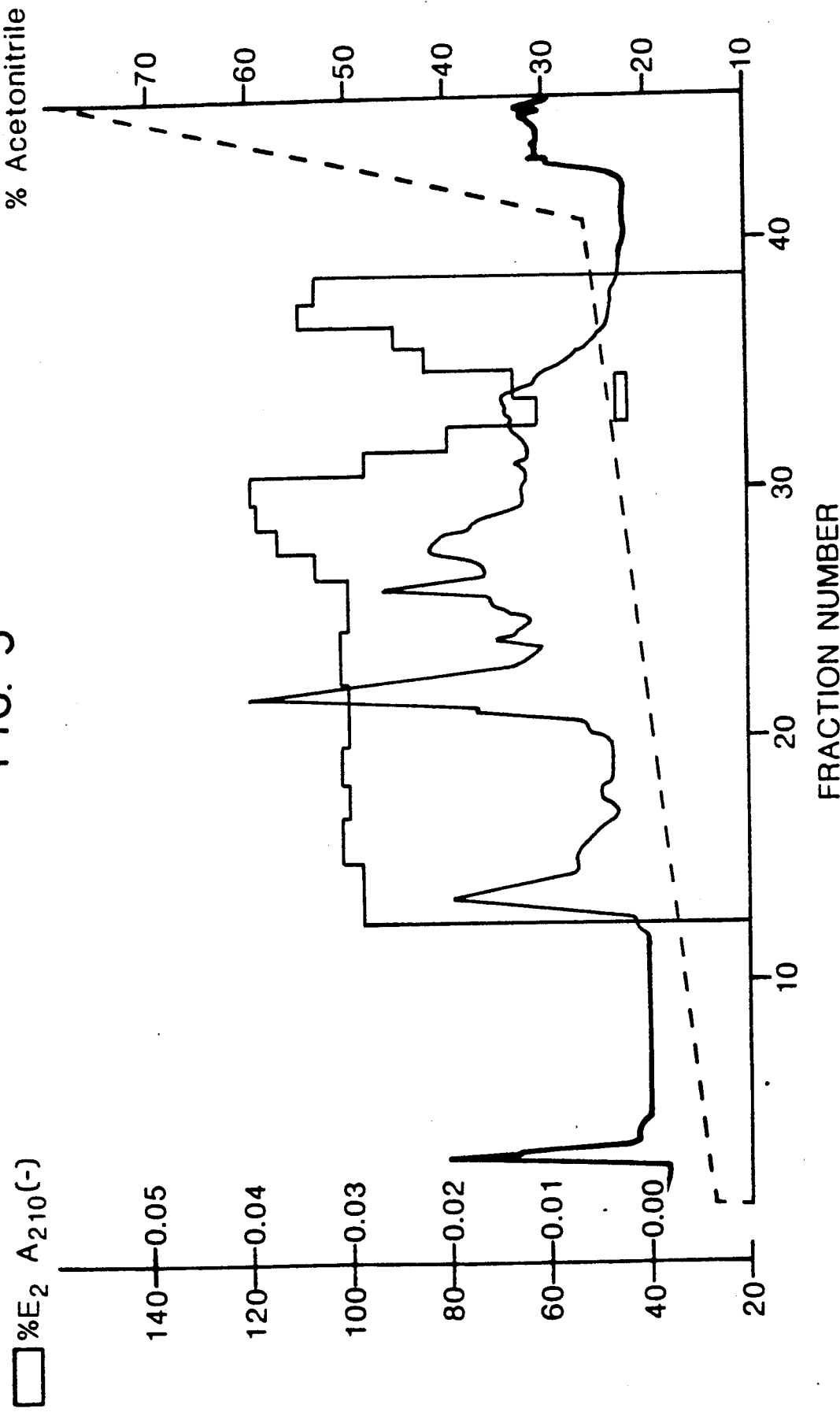

The pooled fractions following dilution are pumped onto a Vydac $1 \times 25$ cm $5\mu$, $C_4$ column. The proteins are eluted from this column using a linear gradient of acetonitrile in the 0.1% TEAP (triethylamine phosphate) solvent system. The linear gradient is adjusted to change from 14 to 26% of acetonitrile over a period of 120 minutes at a flow rate of 3 ml/min at room temperature and a back pressure of about 1020 psig. The active fractions are denoted by the black bar in FIG. 3.

Figure 4:
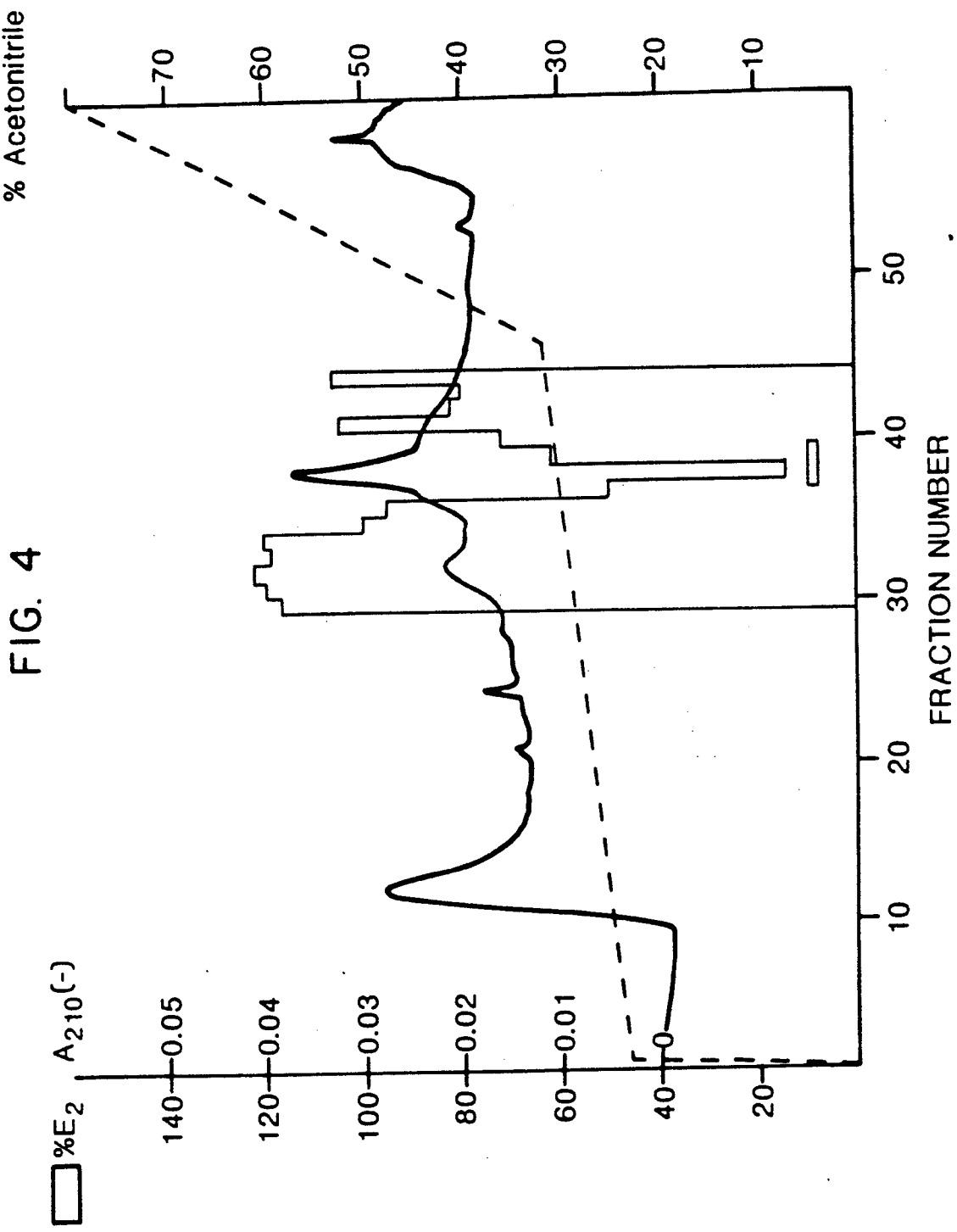

The active fractions are again pooled, diluted with 0.2M acetic acid and pumped onto a similar Vydac $5\mu$, $1 \times 25$ cm $C_4$ column. This time the absorbed material is eluted using an acetonitrile/0.1% TFA solvent system, with a linear gradient from 23 to 32% acetonitrile being effected over 90 minutes using a flow rate of 1 ml per minute. The separation process was carried out at room temperature and with a back pressure of about 330 psig. The fractions collected are again subjected to bioassay in the manner indicated previously and bioactivity is located at fractions 37–39, as shown in FIG. 4. This zone of activity closely mirrors the highest UV absorbing peak, and it is concentrated using a Vydac $5\mu$ $0.45 \times 25$ cm $C_4$ column and a linear gradient of from 0 to 80% acetonitrile over 80 min. in a 0.1% TFA solvent system at a flow rate of 1 ml for each 2 minutes.

The bioassay which is used is one for the inhibition of aromatase which is the central enzyme that produces the female sex hormones, particularly estrogens. Estrogens are produced by the operation of aromatase on the substrate androstenedione. It is known that in the granulosa cells, follicle stimulating hormone (FSH) is necessary to stimulate the production of estrogens by aromatase; therefore, the neutralization of FSH will prevent the production of estrogens. The following procedures are used for the bioassays in Immature female rats are each injected subcutaneously with 3% DES (diethylsilbestrol) in sesame oil, an amount of about 10 milligrams, and after four days the rats are sacrificed and the ovaries are dissected. The ovaries are suspended in a mixture of DMEM (Delbecco Modified Eagle's Medium) and Hams F12 (1:1) and supplemented with 40 micrograms per milliliter gentamicine and 0.1 microgram per milliliter fungizone. The follicles are then punctured with 27-gauge needles using a stereomicroscope, and the cells which are obtained are centrifuged. The supernatent liquid is discarded, and the cells are washed twice with fresh medium. The viability of the cells which are obtained are determined by Trypan blue stain, and about 80% viability is normally obtained Between about $5-6 \times 10^4$ viable cells are plated to each well in a 96-well plastic culture plate using a volume of about 100 microliters of medium for each well. Ovine FSH and androstenedione are then added so that each well has a final concentration of about 20 nanograms per milliliter of oFSH and about $5 \times 10^{-7}$M of androstenedione. The samples for the bioassay are then added immediately in about 100 microliters of medium for each well so that the total being incubated is about 200 microliters in each well. Incubation is carried out for about 72 hours at 37° C. in a 5% carbon dioxide and 95% air atmosphere. The medium is harvested and is measured for estradiol ($E_2$) by radioimmunoassay (RIA). As previously indicated, the FSH-IP neutralizes the effect of FSH and therefore substantially lowers the amount of estradiol which is produced by the granulosa cells.

It is postulated that the dominant follicle, that is, the ovarian follicle that is selected for each cycle, has a mechanism by which it manufactures IGF (insulin-like growth factor) and that IGF neutralizes the FRP so that it is no longer able to block the effect of FSH on the production of estradiol. The remaining primordial follicles, namely the follicles that do not develop, do not manufacture IGF but continue to manufacture FSH-IP, and as a result these follicles do not mature because the FSH is neutralized by the FSH-IP that is produced.

To test the foregoing theory, additional use of the afore-described granulosa cell assay is employed. The assays are first repeated using IGF-I with serial dilutions of from 0 through 22.4 picomoles of IGF-I and a dose response curve is plotted based upon the RIA of $E_2$ which shows a fairly flat line at a level equal to about 100% of control, with a slight gradual rise occurring at concentrations greater than about 1.4 picomoles of the IGF-I. The assays are repeated using IFG-II, and generally similar results are obtained. Then, both assays are repeated with each of the eight serial dilutions of IGF being combined with a constant 4.8 picomoles of the FSH-IP. The results for both of the assays with IGF-I and IGF-II are consistent with the postulation showing a substantial reduction in the amount of estradiol produced (at a level of about 20% of the control) when the particular assay contains about 5.6 picomoles of the IGF or less. At levels of greater than 5.6 picomoles of the IGF compound, the estradiol production returns to substantially that of the control. The foregoing results are consistent with the theory that when sufficient IGF is available, it will tie up the FSH-IP and prevent its neutralizing effect upon FSH, resulting in the production of estradiol by the granulosa cells.

The invention provides methods of contraception by the administration of effective amounts of mammalian FSH-IP, which can be economically produced by synthetic methods. The nomenclature used to define the peptides is that specified by Schroder & Lubke, "The Peptides", Academic Press (1965), wherein in accordance with conventional representation the residue having the free alpha-amino group at the N-terminus appears to the left and the residue having the alpha-carboxyl group at the C-terminus to the right. Where the amino acid residue has isomeric forms, it is the L-form of the amino acid that is represented.

The molecular weight of the pure protein from the separation procedure following the final reverse-phase HPLC step is determined to be about 50,000 kD using NaDodSO$_4$ PAGE. Table I shows the approximate amino acid composition of the protein. The analysis shown is based on the above molecular weight and the fact that it is glycosolated; it indicates that the protein contains approximately 265 amino acid residues. Moreover, the compositions obtained from 2 different batches agree well, which is further evidence of the high purity of the protein.

TABLE I

AMINO ACID COMPOSITION OF FSH-INHIBITING PROTEIN (FSH-IP)
(2 different preparations)

| | Batch No. 1 | Batch No. 2 | average | integer |
|---|---|---|---|---|
| Asx | 22.84 | 23.03 | 22.94 | (23) |
| Thr | 10.46 | 10.71 | 10.59 | (11) |
| Ser | 19.22 | 19.20 | 19.21 | (20) |
| Glx | 27.41 | 27.21 | 27.34 | (27) |
| Pro | 24.31 | 23.78 | 24.05 | (24) |
| Gly | 26.55 | 26.15 | 26.35 | (26) |
| Ala | 21.50 | 21.46 | 21.48 | (21) |
| Cys | 13.19 | 13.21 | 13.20 | (14) |
| Val | 11.40 | 11.63 | 11.52 | (12) |
| Met | 3.42 | 3.54 | 3.48 | (3) |
| Ile | 5.75 | 5.94 | 5.85 | (6) |
| Leu | 19.21 | 19.10 | 19.11 | (19) |
| Tyr | 7.79 | 7.81 | 7.80 | (8) |
| Phe | 5.66 | 5.77 | 5.72 | (6) |
| His | 6.14 | 6.30 | 6.22 | (6) |
| Trp | 0 | 0 | 0 | (0) |
| Lys | 19.03 | 18.94 | 18.99 | (19) |
| Arg | 20.24 | 20.17 | 20.21 | (20) |
| | | | | 265 |

Values represent residues/molecule determined from 24 hour hydrolysates of 5-10 pmoles of protein and are not corrected for hydrolysis losses. These values are consistent with the molecule being between about 260 and 270 residues in length.

By sequencing the purified peptide, the following amino terminal sequence was established: Gly-Ser-Gly-Ala-Val-Gly-Thr-Gly-Pro-Val-Val-Arg-Cys-Glu-Pro-Cys-Asp-Ala-Arg-Ala-Leu-Ala-Gln-Cys-Ala-Pro-Pro-Pro -Ala-Ala-Pro-Pro-Cys-Ala-Glu-Leu-Val-Arg-Glu-Pro-Gly-Cys-. Antibodies are raised in rabbits against a synthetic dodecapeptide representing the amino terminal sequence of the FSH-IP. The antisera recognize the synthetic peptide and the FSH-IP on an equimolar basis and are capable of inhibiting the mitogenic activity of the native protein in vitro. Amino terminal-directed antibodies to FSH-IP are obtained by immunizing three month old male and female white New Zealand rabbits with the synthetic dodecapeptide to which Tyr has been added at the C-terminus, namely: H-Gly-Ser-Gly-Ala-Val-Gly-Thr-Gly-Pro-Val-Val-Arg-Tyr-OH. The antigen is coupled to BSA by a bisdiazotized benzidine(BDB) linkage over a time of 2 hours at 4° C. The reaction mixture is dialized to remove low molecular weight material, and the retentate is frozen in 2 ml aliquots in liquid nitrogen and stored at −20° C. Animals are immunized with the equivalent of 1 mg of the peptide antigen according to the procedure of Benoit et al. *P.N.A.S. USA*, 79, 917-921 (1982). At three week intervals, the animals are boosted by injections of 200 μg of the antigen peptide and bled ten to fourteen days later. After the third boost, antiserum is examined for its capacity to bind radioiodinated antigen peptide prepared by the chloramine-T method and purified by CMC-ion exchange column chromatography using 0.2M ammonium acetate pH=6.5 for elution of the iodinated antigen peptide.

A radioimmunoassay is established with the antisera and serum from subsequent bleeds from the same rabbits. The native protein is recognized by the antibodies on an equimolar basis as compared to the synthetic peptide antigen. The sensitivity of the RIA enables the detection of 500 pg (about 30 fmol) of FSH-IP.

In preliminary experiments, it is shown that the antibodies are capable of partially neutralizing the biological activity of the FSH-IP upon rat granulosa cells in vitro. It is found likely that substantially all activity can be neutralized when higher amounts of antibodies are used. It is believed that immunoaffinity or affinity chromatography can also be applied to achieve the purification of FSH-IP.

Using the RIA, it is demonstrated that rat granulosa cells in monolayer culture release the protein into the culture medium. This release is stimulated by short term incubation (4h) of cells with depolarizing agents, such as 50 mM KCl (3-fold stimulation over control). These data suggest that FSH-IP is actively secreted from the granulosa cells.

From presently available evidence, it is most likely that there is internal disulfide-bonding between cysteine residues of the chain. Mammalian FSH-IP polypeptides produced by recombinant DNA techniques are inherently biologically active, perhaps because the three-dimensional structure which the FSH-IP assumes within cells is the structure recognized by the receptor. The three-dimensional structure which the molecule assumes through natural folding and through hydrophobic and hydrophilic interactions with aqueous media may promote desired bonding or non-bonding between cysteine residues. Also, enzymatic regulatory mechanisms within cells may help to ensure desired disulfide bonding or non-bonding, either by preventing bonding or by directing disulfide bonding between particular cysteine residues. Enzymes might also cleave "incorrect" bonding to enable the molecule to reorientate itself and assume the correct natural structure. Cysteine residues that are not internally bonded may be disulfide-bonded to free cysteine moieties. It may also be that the three-dimensional structure of the molecule is such that random bonding or non-bonding of cysteine residues either with each other or to free cysteines does not substantially affect the biological structure of the protein molecule.

To synthesize a protein having the mammalian FSH-IP amino acid residue sequence by recombinant DNA, a double-stranded DNA chain which encodes FSH-IP is synthetically constructed. The segment of the DNA chain that encodes FSH-IP is, of course, designed according to the genetic code; however, because of the degeneracy of the genetic code, a wide variety of codon combinations can be selected to form the DNA chain that encodes the product polypeptide. It is known that certain particular codons are more efficient for polypeptide expression in certain types of organisms, and the selection of codons preferably is made according to those codons which are most efficient for expression in the type of organism which is to serve as the host for the recombinant vector. However, any correct set of codons will encode the desired product, even if slightly less efficiently. Codon selection may also depend upon vector construction considerations; for example, it may be necessary to avoid placing a restriction site in the DNA chain if, subsequent to inserting the synthetic DNA chain, the vector is to be manipulated using the restriction enzyme that cleaves at such a site. Also, it is necessary to avoid placing restriction sites in the DNA chain if the host organism which is to be transformed with the recombinant vector containing the DNA chain is known to produce a restriction enzyme that would cleave within the DNA chain.

In addition to the FSH-IP-encoding sequences, the DNA chain that is synthesized may contain additional sequences depending upon vector construction considerations. Typically, the DNA chain is synthesized with linkers at its ends to facilitate insertion into restriction sites within a cloning vector. The DNA chain may be constructed so as to encode the FSH-IP amino acid sequences as a portion of a fusion polypeptide; and if so, it will generally contain terminal sequences that encode amino acid residue sequences that serve as proteolytic processing sites, whereby the FSH-IP polypeptide may be proteolytically cleaved from the remainder of the fusion polypeptide. The terminal portions of the synthetic DNA chain may also contain appropriate start and stop signals.

To assemble a FSH-IP-encoding DNA chain, oligonucleotides are constructed by conventional methods, such as procedures described in T. Manatis et al., *Cold Spring Harbor Laboratory Manual*, Cold Spring Harbor, N.Y. (1982) (hereinafter, CSH). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotides overlap, associating with each other through hydrogen bonding between complementary base pairs and thereby forming double stranded chains, in most cases with gaps in the strands. Subsequently, the gaps in the strands are filled in, and oligonucleotides of each strand are joined end to end with nucleotide triphosphates in the presence of appropriate DNA polymerases and/or with ligases.

As an alternative to construction of a synthetic DNA chain through oligonucleotide synthesis, the cDNA corresponding to FSH-IP that was cloned to deduce the complete structure of FSH-IP may be used. As mentioned hereinbefore broadly, a cDNA library or an expression library is produced in a conventional manner by reverse transcription from messenger RNA (mRNA) from a suitable FSH-IP-producing mammalian cell line. To select clones containing FSH-IP sequences, hybridization probes (preferably mixed probes to accommodate the degeneracy of the genetic code) corresponding to portions of the FSH-IP protein are produced and used to identify clones containing such sequences. Screening of such an expression library with FSH-IP antibodies may also be used, either alone or in conjunction with hybridization probing, to identify or confirm the presence of FSH-IP-encoding DNA sequences in cDNA library clones which are expressing FSH-IP. Such techniques are taught, for example in CSH, supra.

The double-stranded FSH-IP-encoding DNA chain is constructed or modified with insertion into a particular appropriate cloning vector in mind. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as *E. Coli*, the DNA chain will be inserted 3' promoter sequence, a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For insertion into a eukaryotic cell, such as a yeast cell or a cell line obtained from a higher animal, the FSH-IP-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col E1, pCR1, RP4 and lambda-phage, are available for inserting a DNA chain of the length which encodes FSH-IP with substantial assurance of at least some expression of the encoded polypeptide. Typically, such vectors are constructed or modified to have a unique restriction site(s) appropriately positioned relative to a promoter, such as the lac promoter. The DNA chain may be inserted with appropriate linkers into such a restriction site, with substantial assurance of production of FSH-IP in a prokaryotic cell line transformed with the recombinant vector. To assure proper reading frame, linkers of various lengths may be provided at the ends of the FSH-IP-encoding sequences. Alternatively, cassettes, which include sequences, such as the 5' region of the lac Z gene (including the operator, promoter, transcription start site, Shine Delgarno sequence and translation initiation signal), the regulatory region from the tryptophane gene (trp operator, promoter, ribosome binding site and translation initiator), and a fusion gene containing these two promoters called the trp-lac or commonly called the Tac promoter are available into which the synthetic DNA chain may be conveniently inserted and then the cassette inserted into a cloning vector of choice.

Similarly, eukaryotic transformation vectors, such as, the cloned bovine papilloma virus genome, the cloned genomes of the murine retroviruses, and eukaryotic cassettes, such as the pSV-2 gpt system (described by Mulligan and Berg, *Nature* 277, 108–114, 1979) the Okayama-Berg cloning system (*Mol. Cell Biol.* 2, 161–170, 1982), the expression cloning vector recently described by Genetics Institute (*Science* 228, 810–815, 1985), are available which provide substantial assurance of at least some expression of FSH-IP in the transformed eukaryotic cell line.

As previously mentioned, a convenient way to ensure production of FSH-IP or a polypeptide of a similar length is to produce the polypeptide initially as a segment of a gene-encoded fusion polypeptide. In such case, the DNA chain is constructed so that the expressed polypeptide has enzymatic processing sites flanking the FSH-IP amino acid residue sequences. A FSH-IP-encoding DNA chain may be inserted, for example, into the beta-galactosidase gene for insertion into *E. Coli*, in which case, the expressed fusion polypeptide is subsequently cleaved with proteolytic enzymes to release the FSH-IP from beta-galactosidase peptide sequences.

An advantage of inserting the FSH-IP-encoding sequence is expressed so that the FSH-IP sequence is expressed as a cleavable segment of a fusion polypeptide, e.g., as the FSH-IP peptide sequence fused within the beta-galactosidase peptide sequence, is that the endogenous polypeptide into which the FSH-IP sequence is inserted is generally rendered non-functional, thereby facilitating selection for vectors encoding the fusion peptide.

The FSH-IP peptide may also be reproduced in yeast using known recombinant DNA techniques. For example, plasmid pFSH-IP, amplified in a pFSH-IP-producing *E. Coli* clone, is isolated and cleaved with Eco RI and Sal I. This digested plasmid is electrophoresed on an agarose gel allowing for the separation and recovery of the amplified bFSH-IP insert. The insert is inserted into the plasmic pYEp, a shuttle vector which can be used to transform both *E. Coli* and *Saccharomyces cerevisiae* yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against FSH-IP, demonstrating that a peptide containing FSH-IP peptide segments is expressed within the yeast cells.

The production of FSH-IP can be carried out in both prokaryotic and eukaryotic cell lines to provide polypeptides for biological and therapeutic use. While FSH-IP synthesis is easily demonstrated using either bacteria or yeast cell lines, the synthetic genes should be insertable for expression in cells of higher animals, such as mammalian tumor cells. Such mammalian cells may be grown, for example, as peritoneal tumors in host animals, and FSH-IP harvested from the peritoneal fluid.

Although the above examples demonstrate that FSH-IP can be synthesized through recombinant DNA techniques, the examples do not purport to have maximized FSH-IP production. It is expected that subsequent selection of more efficient cloning vectors and host cell lines will increase the yield of FSH-IP. Known gene amplification techniques for both eukaryotic and prokaryotic cells may be used to increase production of FSH-IP. Secretion of the gene-encoded polypeptide from the host cell line into the culture medium is also considered to be an important factor in obtaining synthetic FSH-IP in large quantities.

The availability of mammalian FSH-IP peptides permit their use as mammalian contraceptives for both males and females. These peptides should also be useful in the treatment of other conditions which are caused by an overabundance of FSH or estrogen, for example, endometriosis and certain types of breast cancer. Administration of substantially pure monoclonal antibodies to FSH-IP peptides have potential therapeutic applications to treat cases of infertility.

Substantially pure FSH-IP polypeptides can be routinely obtained having significantly higher purity than FSH-IP polypeptides that are extracted from mammalian tissues and follicular fluid. FSH-IP polypeptides constitute only very minor constituents of normal mammalian tissues and thus are present only in very impure form, relative to other native polypeptides also present. Recombinant DNA techniques, for example, can be used to generate organisms or cell lines that produce the heterologous polypeptide in significantly higher proportions relative to total protein, in the cellular material and/or their secretions, than the proportions at which native FSH-IP polypeptides are present in mammalian tissue. Because the starting material from which such synthetic FSH-IP polypeptides are isolated has a substantially greater concentration of the heterologous polypeptide, purification techniques can fairly simply produce more highly purified FSH-IP polypeptide fractions. Using such isolation techniques, it is possible to routinely obtain FSH-IP polypeptides which are at least about 95% pure (by weight of total proteins) and which is herein referred to as substantially pure.

The peptides should be administered under the guidance of a physician, and pharmaceutical compositions will usually contain the peptide in conjunction with a conventional, pharmaceutically-acceptable carrier. For contraceptive treatment, substantially pure synthetic FSH-IP or the nontoxic salts thereof, combined with a pharmaceutically acceptable carrier to form a pharmaceutical composition, are administered to mammals, including humans, either intravenously, subcutaneously, intramuscularly or orally. The required dosage will vary with the particular treatment and with the duration of desired treatment; however, it is anticipated that dosages between about 10 micrograms and about 1 milligram per kilogram of body weight per day will be used for therapeutic and for contraceptive treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver FSH-IP over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain FSH-IP or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

For purposes of this application, mammalian FSH-IP peptides should be considered to constitute peptides having the amino acid residue sequences set forth hereinbefore as well as naturally occurring amino acid sequence variants of other mammalian species and fragments of the foregoing having equivalent biological activity. Unless otherwise stated hereinbefore, all percentages are volume percents.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, with respect to most polypeptides, biologically active fragments, shortened either at the C-terminus or at the N-terminus, can be employed instead of the entire peptide.

Particular features of the invention are emphasized in the claims which follow.

What is claimed is:

1. A method of treating endometriosis comprising administering a daily amount of between about 10 micrograms and about 1 milligram per kilogram body weight of a protein having the peptide sequence: G A S S G G L G P V V R C E P C D A R A L A Q C A P P P A V C A E L V R E P G C G C C L T C A L S E G Q P C G I Y T E R C G S G L R C Q P S P D E A R P L Q A L L D G R G L C V N A S A V S R L R A Y L L P A P P A P G N A S E S E E D R S A G S V E S P S V S S T H R V S D P K F H P L H S K I I I K K G H A K D S Q R Y K V D Y E S Q S T D T Q N F S S E S K R E T E Y G P C R R E M E D T L N H L K F L N V L S P R G V H I P N C D K K G F Y K K K Q C R P S K G R K R G F C W C V D K Y G Q P L P G Y T T K G K E D V H C Y S M Q S K.

2. A method of achieving contraception in mammals, which method comprises administering an effective amount of a substantially pure mammalian FSH-inhibiting protein which has the polypeptide sequence: G A S S G G L G P V V R C E P C D A R A L A Q C A P P P A V C A E L V R E P G C G C C L T C A L S E G Q P C G I Y T E R C G S G L R C Q P S P D E A R P L Q A L L D G R G L C V N A S A V S R L R A Y L L P A P P A P G N A S E S E E D R S A G S V E S P S V S S T H R V S D P K F H P L H S K I I I K K G H A K D S Q R Y K V D Y E S Q S T D T Q N F S S E S K R E T E Y G P C R R E M E D T L N H L K F L N V L S P R G V H I P N C D K K G F Y K K K Q C R P S K G R K R G F C W C V D K Y G Q P L P G Y T T K G K E D V H C Y S M Q S K.

* * * * *

UNITED STATES PATENT AND TRADEMARK OFFICE
CERTIFICATE OF CORRECTION

PATENT NO. : 5,037,805
DATED : 8/6/91
INVENTOR(S) : LING, Nicholas C.

It is certified that error appears in the above-identified patent and that said Letters Patent is hereby corrected as shown below:

On the title page:
TITLE: Change the title to: --Methods of Contraception and Treatment of Endometriosis--. Column 1, line 1, change title to read --Methods of Contraception and Treatment of Endometriosis--. Column 5, line 15, after "obtained" insert --.-- (period). Column 9, line 10, after "3" insert --of a--.

Signed and Sealed this

Twenty-ninth Day of December, 1992

Attest:

DOUGLAS B. COMER

Attesting Officer      Acting Commissioner of Patents and Trademarks